US012678468B2

(12) United States Patent
Karpf

(10) Patent No.: US 12,678,468 B2
(45) Date of Patent: Jul. 14, 2026

(54) METHOD FOR REDUCING THE POPULATION OF AT LEAST ONE INTESTINAL AND/OR GASTROINTESTINAL BACTERIA SPECIES COMPRISING BACTERIOPHAGES, AND BACTERIOPHAGES AND THE USE THEREOF

(71) Applicant: Oxana Karpf, Saarbruecken (DE)

(72) Inventor: Oxana Karpf, Saarbruecken (DE)

( * ) Notice: Subject to any disclaimer, the term of this patent is extended or adjusted under 35 U.S.C. 154(b) by 519 days.

(21) Appl. No.: 18/034,746

(22) PCT Filed: Oct. 19, 2021

(86) PCT No.: PCT/EP2021/078868
§ 371 (c)(1),
(2) Date: May 1, 2023

(87) PCT Pub. No.: WO2022/096254
PCT Pub. Date: May 12, 2022

(65) Prior Publication Data
US 2023/0398162 A1      Dec. 14, 2023

(30) Foreign Application Priority Data
Nov. 3, 2020    (DE) ..................... 10 2020 128 879.4

(51) Int. Cl.
| | |
|---|---|
| *A61K 31/407* | (2006.01) |
| *A61B 5/00* | (2006.01) |
| *A61K 31/546* | (2006.01) |
| *A61K 35/76* | (2015.01) |
| *C12N 7/00* | (2006.01) |
| *C12Q 1/18* | (2006.01) |
| *C12Q 1/689* | (2018.01) |

(52) U.S. Cl.
CPC ............... *A61K 35/76* (2013.01); *C12N 7/00* (2013.01); *C12N 2795/00032* (2013.01)

(58) Field of Classification Search
CPC . Y02A 50/30; A61B 10/04; A61B 2010/0061; C12Q 1/18; C12Q 1/689
See application file for complete search history.

(56) References Cited

FOREIGN PATENT DOCUMENTS

| | | | |
|---|---|---|---|
| CA | 3088786 A1 | | 7/2019 |
| EP | 2958575 B1 | | 4/2019 |
| JP | 2020143119 A | | 9/2020 |
| WO | 2014133289 A1 | | 9/2014 |
| WO | 2019140534 A1 | | 7/2019 |
| WO | WO2019140534 | * | 7/2019 |
| WO | 2021151759 A1 | | 8/2021 |

OTHER PUBLICATIONS

George Tetz et al. "Bacteriophages as New Human Viral Pathogens" Microorganisms, vol. 6, No. 2, Jun. 16, 2018 (Jun. 16, 2018), pp. 1-12.
Sarkar Amar et al. "The Microbiome in Psychology and Cognitive Neuroscience" Trends in Cognitive Sciences, Elsevier Science, Oxford, GB, vol. 22, No. 7, Jun. 12, 2018 (Jun. 12, 2018), pp. 611-636.
Vandenheuvel Dieter et al. "Bacteriophage Therapy: Advances in Formulation Strategies and Human Clinical Trials" Annual Review of Virology, USA. vol. 2. No. 1. Nov. 9, 2015 (Nov. 9, 2015). pp. 599-618.
International Search Report, Corresponding to EP/PCT2021/078868, dated Feb. 2, 2022.
Lu, T. et al., Dispersing Biofilms with Engineered Enzymatic Bacteriophage, PNAS, 2007, 104(27):11197-11202.
Pei, R. et al., Inhibition of Biofilm Formation by T7 Bacteriophages Producing Quorum-Quenching Enzymes, Applied and Environmental Microbiology, 2014, 80(17):5340-5348.
Japan Patent Office, Notice of Reasons for Rejection (Translation), Application No. 2023-527006, Nov. 5, 2024, 7 pages.
PCT International Preliminary Report on Patentability, PCT/EP2021/078868, May 19, 2023, 10 pages.
Annex 1—Gomez-Ochoa, Sergio Alejandro, et al. "Efficacy of phage therapy in preclinical models of bacterial infection: a systematic review and meta-analysis." The Lancet Microbe 3.12 (2022): e956-e968.
Annex 2—Pirnay, Jean-Paul, et al. "Personalized bacteriophage therapy outcomes for 100 consecutive cases: a multicentre, multinational, retrospective observational study." Nature microbiology 9.6 (2024): 1434-1453.
Annex 3—Sawa, Teiji, Kiyoshi Moriyama, and Mao Kinoshita. "Current status of bacteriophage therapy for severe bacterial infections." Journal of Intensive Care 12.1 (2024): 44.
Annex 4—Kim, Minyoung Kevin, et al. "Bacteriophage therapy for multidrug-resistant infections: current technologies and therapeutic approaches." The Journal of Clinical Investigation 135.5 (2025).
Annex 5—Zhang, Youying, et al. "Bacteroides species differentially modulate depression-like behavior via gut-brain metabolic signaling." Brain, behavior, and immunity 102 (2022): 11-22.
Annex 6—Zhao, Jia, et al. "The gut microbiota-brain connection: insights into major depressive disorder and bipolar disorder." Frontiers in Psychiatry 15 (2024): 1421490.
Annex 7—Luqman, Ameer, et al. "Mood and microbes: a comprehensive review of intestinal microbiota's impact on depression." Frontiers in psychiatry 15 (2024): 1295766.

(Continued)

*Primary Examiner* — Barry A Chestnut
(74) *Attorney, Agent, or Firm* — Quarles & Brady LLP

(57) ABSTRACT

The invention relates to a method for reducing the population of at least one intestinal and/or gastrointestinal species of bacteria, the method comprising the following steps:
  a) providing a biological sample containing bacteria of at least one intestinal and/or gastrointestinal species of bacteria, the intestinal and/or gastrointestinal species of bacteria directly or indirectly influencing a psychological, neurodegenerative and/or neurological illness and/or disorder of a host organism; and
  b) providing bacteriophages of at least one species of bacteriophages that are specific to the intestinal and/or gastrointestinal species of bacteria and that comprise at least one nucleic acid functionally associated with a promotor and/or a regulatory element; and
  c) contacting and incubating the biological sample with the bacteriophages, the incubation continuing until the population of the intestinal and/or gastrointestinal species of bacteria has been reduced by at least 70%.

8 Claims, No Drawings

(56) References Cited

OTHER PUBLICATIONS

Annex 8—Wasen, Caroline, et al. "Bacteroidota inhibit microglia clearance of amyloid-beta and promote plaque deposition in Alzheimer's disease mouse models." Nature Communications 15.1 (2024): 3872.

Annex 9—Li, Hui, et al. "Gut microbiota changes in patients with Alzheimer's disease spectrum based on 16S rRNA sequencing: a systematic review and meta-analysis." Frontiers in Aging Neuroscience 16 (2024): 1422350.

Annex 10—Jimenez-García, Ana Maria, Maria Villarino, and Natalia Arias. "A systematic review and meta-analysis of basal microbiota and cognitive function in Alzheimer's disease: A potential target for treatment or a contributor to disease progression?." Alzheimer's & Dementia: Diagnosis, Assessment & Disease Monitoring 16.4 (2024): e70057.

Annex 11—Noori, Maryam, et al. "Helicobacter pylori infection contributes to the expression of Alzheimer's disease-associated risk factors and neuroinflammation." Heliyon 9.9 (2023).

Annex 12—Murros, Kari E., et al. "Desulfovibrio bacteria are associated with Parkinson's disease." Frontiers in Cellular and Infection Microbiology 11 (2021): 652617.

Annex 13—Ritz, Nathaniel L., et al. "The gut virome is associated with stress-induced changes in behaviour and immune responses in mice." Nature Microbiology 9.2 (2024): 359-376.

Annex 14—Talarico, Francesca, et al. "The effects of stress on gut virome: Implications on infectious disease and systemic disorders." MicrobiologyOpen 13.5 (2024): e1434.

Annex 15—Rasmussen, Torben Sølbeck, et al. "Overcoming donor variability and risks associated with fecal microbiota transplants through bacteriophage-mediated treatments." Microbiome 12.1 (2024): 119.

Annex 16—Du, Jiwen, et al. "Association of Helicobacter pylori infection with the risk of neurodegenerative disorders: a systematic review and meta-analysis." Frontiers in Medicine 12 (2025): 1573299.

Annex 17—Zhu, Juan, et al. "Altered fecal microbiota signatures in patients with anxiety and depression in the gastrointestinal cancer screening: a case-control study." Frontiers in Psychiatry 12 (2021): 757139.

Annex 18—Li, Jiayu, et al. "Bifidobacterium: a probiotic for the prevention and treatment of depression." Frontiers in Microbiology 14 (2023): 1174800.

Annex 19—Caso, Javier R., et al. "Gut microbiota, innate immune pathways, and inflammatory control mechanisms in patients with major depressive disorder." Translational psychiatry 11.1 (2021): 645.

Annex 20—Pisani, Flavio, et al. "The mechanistic pathways of periodontal pathogens entering the brain: The potential role of treponema denticola in tracing Alzheimer's disease pathology." International journal of environmental research and public health 19.15 (2022): 9386.

Annex 21—Wan, Jason, and Hongkuan Fan. "Oral microbiome and Alzheimer's disease." Microorganisms 11.10 (2023): 2550.

Annex 22—Kaiyrlykyzy, Aiym, et al. "Study of gut microbiota alterations in Alzheimer's dementia patients from Kazakhstan." Scientific reports 12.1 (2022): 15115.

Annex 23—Ou, Hsun, et al. "Association between antibiotic treatment of Chlamydia pneumoniae and reduced risk of Alzheimer dementia: a nationwide cohort study in Taiwan." Frontiers in Aging Neuroscience 13 (2021): 701899.

Annex 24—Troci, Alba, et al. "Disease-and stage-specific alterations of the oral and fecal microbiota in Alzheimer's disease." PNAS nexus 3.1 (2024): pgad427.

Annex 25—Catumbela, Celso SG, et al. "Clinical evidence of human pathogens implicated in Alzheimer's disease pathology and the therapeutic efficacy of antimicrobials: An overview." Translational Neurodegeneration 12.1 (2023): 37.

Annex 26—Bai, Xue-Bing, et al. "Oral pathogens exacerbate Parkinson's disease by promoting Th1 cell infiltration in mice." Microbiome 11.1 (2023): 254.

Annex 27—Grahl, Matheus VC, et al. "Could the Urease of the Gut Bacterium Proteus mirabilis Play a Role in the Altered Gut-Brain Talk Associated with Parkinson's Disease?." Microorganisms 11.8 (2023): 2042.

Annex 28—Rojas-Velazquez, David, et al. "Understanding Parkinson's: The microbiome and machine learning approach." Maturitas 193 (2025): 108185.

Annex 29—Romano, Stefano, et al. "Meta-analysis of the Parkinson's disease gut microbiome suggests alterations linked to intestinal inflammation." npj Parkinson's Disease 7.1 (2021): 27.

Annex 30—Zhang, Xuxiang, Beisha Tang, and Jifeng Guo. "Parkinson's disease and gut microbiota: from clinical to mechanistic and therapeutic studies." Translational Neurodegeneration 12.1 (2023): 59.

Annex 31—Li, Zhe, et al. "Gut bacterial profiles in Parkinson's disease: a systematic review." CNS neuroscience & therapeutics 29.1 (2023): 140-157.

Annex A—Eckstein, Simone, et al. "Isolation and characterization of lytic phage TUN1 specific for Klebsiella pneumoniae K64 clinical isolates from Tunisia." BMC microbiology 21.1 (2021): 186.

Annex AA—Alam, Mudassir, et al. "Microbiome-based therapies for Parkinson's disease." Frontiers in nutrition 11 (2024): 1496616.

Annex AB—Charitos, Ioannis Alexandros, et al. "The gut microbiota's role in neurological, psychiatric, and neurodevelopmental disorders." Nutrients 16.24 (2024): 4404.

Annex AC—Fan, Hong-Xia, Shuo Sheng, and Feng Zhang. "New hope for Parkinson's disease treatment: Targeting gut microbiota." CNS neuroscience & therapeutics 28.11 (2022): 1675-1688.

Annex AD—Faraji, Navid, et al. "Vagus nerve stimulation and gut microbiota interactions: a novel therapeutic avenue for neuropsychiatric disorders." Neuroscience & Biobehavioral Reviews 169 (2025): 105990.

Annex AE—Jia, Min, et al. "Gut microbiota dysbiosis promotes cognitive impairment via bile acid metabolism in major depressive disorder." Translational psychiatry 14.1 (2024): 503.

Annex AF—Li, Xiang, et al. "Fecal microbiota transplantation attenuates Alzheimer's disease symptoms in APP/PS1 transgenic mice via inhibition of the TLR4-MyD88-NF-KB signaling pathway-mediated inflammation." Behavioral and Brain Functions 21.1 (2025): 2.

Annex AG—Liapis, C. C. ""Pseudoneurotransmission" and gut microbiome-brain communication in neuropsychiatric disorders." Psychiatrike= Psychiatriki (2024).

Annex AH—Yu, Bo, Hang Zhang, and Min Zhang. "Deep learning-based differential gut flora for prediction of Parkinson's." PloS one 20.1 (2025): e0310005.

Annex B—Emslander, Quirin, et al. "Cell-free production of personalized therapeutic phages targeting multidrug-resistant bacteria." Cell chemical biology 29.9 (2022): 1434-1445.

Annex C—Falgenhauer, Elisabeth, et al. "Evaluation of an E. coli cell extract prepared by lysozyme-assisted sonication via gene expression, phage assembly and proteomics." ChemBioChem 22.18 (2021): 2805-2813.

Annex D—Willy, Christian, et al. "Phage therapy in Germany-update 2023." Viruses 15.2 (2023): 588.

Annex E—Würstle, Silvia, et al. "Practical assessment of an interdisciplinary bacteriophage delivery pipeline for personalized therapy of gram-negative bacterial infections." Pharmaceuticals 15.2 (2022): 186.

Annex F—Vogele, Kilian, et al. "Small Antisense DNA-Based Gene Silencing Enables Cell-Free Bacteriophage Manipulation and Genome Replication." ACS Synth. Biol. (2021) 10, 459-465.

Annex G—Ma, Yinghua, et al. "Epsilon toxin-producing Clostridium perfringens colonize the multiple sclerosis gut microbiome overcoming CNS immune privilege." The Journal of clinical investigation 133.9 (2023).

Annex H—Huynh, Vy A., et al. "Desulfovibrio bacteria enhance alpha-synuclein aggregation in a Caenorhabditis elegans model of Parkinson's disease." Frontiers in Cellular and Infection Microbiology 13 (2023): 1181315.

(56)　　　　　References Cited

OTHER PUBLICATIONS

Annex I—Singh, Sudha B., Amanda Carroll-Portillo, and Henry C. Lin. "Desulfovibrio in the gut: the enemy within?." Microorganisms 11.7 (2023): 1772.

Annex K—Liu, Lanxiang, et al. "Gut microbiota and its metabolites in depression: from pathogenesis to treatment." EBioMedicine 90 (2023).

Annex L—Tian, Peijun, et al. "Multi-probiotics ameliorate major depressive disorder and accompanying gastrointestinal syndromes via serotonergic system regulation." Journal of advanced research 45 (2023): 117-125.

Annex M—Schaub, Anna-Chiara, et al. "Clinical, gut microbial and neural effects of a probiotic add-on therapy in depressed patients: a randomized controlled trial." Translational psychiatry 12.1 (2022): 227.

Annex N—Schneider, Else, et al. "Effect of short-term, high-dose probiotic supplementation on cognition, related brain functions and BDNF in patients with depression: a secondary analysis of a randomized controlled trial." Journal of Psychiatry and Neuroscience 48.1 (2023): E23-E33.

Annex O—Dhopatkar, Namrata, et al. "Gastrointestinal symptoms, gut microbiome, probiotics and prebiotics in anorexia nervosa: A review of mechanistic rationale and clinical evidence." Psychoneuroendocrinology 147 (2023): 105959.

Annex P—Góralczyk-Bińkowska, Aleksandra, Dagmara Szmajda-Krygier, and Elżbieta Kozłowska. "The microbiota-gut-brain axis in psychiatric disorders." International journal of molecular sciences 23.19 (2022): 11245.

Sabino, João, Robert P. Hirten, and Jean-Frederic Colombel. "bacteriophages in gastroenterology—from biology to clinical applications." Alimentary pharmacology & therapeutics 51.1 (2020): 53-63.

Cryan, John F., et al. "The gut microbiome in neurological disorders." The Lancet Neurology 19.2 (2020): 179-194.

Office Action, corresponding to KR 10-2023-7018389, dated Dec. 8, 2025.

* cited by examiner

METHOD FOR REDUCING THE POPULATION OF AT LEAST ONE INTESTINAL AND/OR GASTROINTESTINAL BACTERIA SPECIES COMPRISING BACTERIOPHAGES, AND BACTERIOPHAGES AND THE USE THEREOF

CROSS-REFERENCE TO RELATED APPLICATIONS

This application is the U.S. National Stage of PCT/EP2021/078868 with international filing date of Oct. 19, 2021, which published as WO 2022/096254 on May 12, 2022, and which claims priority to German Patent Application No. 10 2020 128 879.4 with filing date of Nov. 3, 2020. The content of each of the above-referenced applications is incorporated herein by reference in its entirety.

The invention relates to a method for reducing the population of at least one intestinal and/or gastrointestinal species of bacteria and to bacteriophages and their use according to the preamble of the independent claims.

It is sufficiently known that the microbiome, i.e., the entirety of all microorganisms populating the gastrointestinal tract, plays a role not only in digestion and the formation of the immune system but also in various other metabolic processes. One reason for this is that about a third of all metabolic products in human and/or animal blood originate from the microbes in the body. Therefore, it is no surprise that more and more studies prove that the microbiome can have an impact on different illnesses far from intestinal and/or gastrointestinal troubles. For instance, studies were able to show that the gut microbiota can impact thinking, feeling, the mood and/or the psyche of an organism, while the precise correlations of this so-called gut-brain axis are not known yet. Hence, the latest research suggests that the communication via the gut-brain axis even goes both ways, which means that the mental condition of an organism also has an impact on its bowel function, whereas, vice-versa, the condition of the intestinal mucosa or the composition of the gut microbiota can influence mental health.

Different options for influencing the gut microbiota and in particular the intestinal and/or gastrointestinal bacteria of the microbiome are known from the current state of the art. For instance, it is known for a probiotic therapy to be applied in order to change and/or influence the type and/or the composition of the bacteria in an organism. Furthermore, it is known for antibiotics to be used as chemical substances, which are currently considered the conventional therapy for humans and animals, to fight and/or change the bacterial colonization. Substances of this kind are characterized by a broad action spectrum since they target molecular structures or molecules of the bacteria that occur in a variety of species of bacteria. Thus, the use of antibiotics naturally reduces and/or eliminates a wide range of bacteria. This has the disadvantage that it also affects the bacteria that benefit, i.e., live in symbiosis with, humans or animals, which can cause consequential damage to humans, animals and/or the environment. It is conceivable that this may lead to a shift in the balance of the microbiome to the advantage of pathogenic microorganisms (e.g., bacteria and/or fungi), which can result in a condition lasting for several months or years with sometimes serious consequences down the line. For instance, it is known that chemical substances used as antibiotics can interact with physiological metabolic processes and can cause the development of allergies against the chemical substance and the consequences of a resulting allergic reaction and even allergic shock syndrome and/or the development of various intolerances, for example. Moreover, in the event of failure of the antibiotic therapy, the same medicinal agent cannot be used again, which means that the therapy is typically switched to another group of antibiotic agents which has an even broader action spectrum and can therefore lead to an even more significant disturbance of the balance of the microbiome including the development of multi-resistant bacteria. Hence, the recommendation is to adhere to a certain latency between antibiotic therapies. Furthermore, it is known for a stool transplant to be carried out, thereby transferring the bacteria mix in the stool of a healthy human or animal to another organism. The stool transplant offers actual improvement of the troubles for a major part of the treated organisms and is additionally suitable for treating dangerous multi-resistant pathogens, which are mostly insusceptible to antibiotic therapy.

However, the therapy options mentioned above are disadvantageous in that they are either accompanied by significant disadvantages or merely lead to an improvement of the situation that typically does not last long. Moreover, the therapies known from the state of the art do not allow one or more species of bacteria to be addressed specifically.

Hence, there is a great and continuously growing demand for addressing, fighting, reducing and/or partially or fully eliminating an intestinal and/or gastrointestinal species of bacteria in a manner that is simple, effective, well-tolerated, non-hazardous to health, low in side effects, cost efficient, targeted and specific. At the same time, a long-term therapy success is required. Hence, the object of the invention is to provide bacteriophages and a method for reducing the population of at least one intestinal and/or gastrointestinal species of bacteria in order to avoid the disadvantages of the state of the art mentioned above and which is characterized by a high efficacy, specificity, tolerability and/or reliability and a simple, low-error, time- and cost-efficient application.

This object is attained in a surprisingly simple but effective manner by a method and by bacteriophages according to the teaching of the independent claims.

According to the invention, a method for reducing the population of at least one intestinal and/or gastrointestinal species of bacteria is proposed, the method comprising the following steps:

a) providing a biological sample containing bacteria of at least one intestinal and/or gastrointestinal species of bacteria, the intestinal and/or gastrointestinal species of bacteria directly or indirectly influencing a psychological, neurodegenerative and/or neurological illness and/or disorder of a host organism; and b) providing bacteriophages of at least one species of bacteriophages that are specific to the intestinal and/or gastrointestinal species of bacteria and that comprise at least one nucleic acid functionally associated with a promotor and/or a regulatory element, the nucleic acid being selected from the group comprising:

i. a nucleic acid sequence coding for at least one antibacterial nucleic acid molecule; and ii. a nucleic acid sequence encoding a nucleic acid molecule that is identical to the nucleic acid molecule encoded by the nucleic acid sequences from i) by at least 50%; and iii. a nucleic acid sequence coding for at least one antibacterial polypeptide; and iv. a nucleic acid sequence encoding a polypeptide that is identical to the polypeptide encoded by the nucleic acid sequences from iii) by at least 50%; and v. a nucleic acid sequence for a fragment of a nucleic acid from i), ii), iii) or iv), the fragment encoding a nucleic acid molecule or a polypeptide; and c) contacting and incubating the biological sample with the bacteriophages, the incubation continuing until the population of the intestinal and/or gastrointestinal species of bacteria has been reduced by at least 70%.

The method according to the invention is based on the idea that the use of bacteriophages specific to the at least one intestinal and/or gastrointestinal species of bacteria allows the population of this at least one intestinal and/or gastrointestinal species of bacteria to be reduced in a reliable, quick, simple, specific and permanent manner. It has been found that the simultaneous host dependency means that other organisms, such as fungi, bacteria, viruses or the like, and/or cells of multi-cell tissue and/or organisms advantageously remain unharmed, which means that they are not damaged, impaired and/or disturbed. The host dependency of the bacteriophages allows the method according to the invention to be repeated at any time without the occurrence of any resistances. As a person skilled in the art knows, simultaneous host dependency occurs if no other species of bacteria that are present in the biological sample and for which the bacteriophage is not specific is reduced in the absence of the intestinal and/or gastrointestinal species of bacteria in question from the biological sample. This also applies to organs and/or tissue of the host organism, i.e., the human and/or animal organism.

In the scope of the invention, it has been found that in order to reduce the population of at least one species of bacteria, it suffices to provide a biological sample containing bacteria of at least one intestinal and/or gastrointestinal species of bacteria and to incubate it with the administered bacteriophages of at least one species of bacteriophages that are specific to the at least one intestinal and/or gastrointestinal species of bacteria.

The term "population" is known to the person skilled in the art and generally refers to the entirety of all individuals of the same species that are present in a certain area of the environment. In the scope of the invention, the population refers to the entirety of the bacteria of at least one intestinal and/or gastrointestinal species of bacteria. The terms "bacterium" and "bacteria" are known to the person skilled in the art as replaceable synonyms and refer to the representatives of one or more species of bacteria.

The term "intestinal and/or gastrointestinal species of bacteria" is known to a person skilled in the art and refers to at least one species of bacteria, preferably 2, 3, 4, 5, 6, 7, 8, 9, 10, 11, 12, 13, 14, 15, 16, 17, 18, 19, 20 or more species of bacteria, that can occur in and/or populates the gastrointestinal tract of the human and/or animal organism, e.g., in the stomach and/or in the intestine. The intestinal and/or gastrointestinal species of bacteria directly or indirectly influences the host organism because of its biology, such as its molecular metabolism and/or its interaction with other species of bacteria, fungi and/or cells, in such a manner that a psychological, neurodegenerative and/or neurological illness and/or disorder is initiated, promoted, manifested and/or exacerbated. A person skilled in the art knows a direct or indirect impact on the host organism. For instance, they can influence the host organism directly by destroying tissue of the host organism or at least emitting a transmitter substance. Furthermore, they can influence the host organism indirectly, for example, by influencing the metabolism, other microorganisms or other processes of the host organism and/or by changing the composition of the gut microbiota. Furthermore, the person skilled in the art understands that while said species of bacteria does not have to have a direct effect in the organism itself in this context, it can conflict with the growth, the biology and/or the survival of a species of bacteria acting opposite and therefore has an indirect effect on the host organism.

The intestinal and/or gastrointestinal species of bacteria is non-exclusively selected from: *Acinetobacter, Actinobacterium, Actinomyces, Actinomycineae, Alistipes, Acidaminococcaceae, Bacillus, Bacteroides, Bacteroidetes, Bartonella, Bifidobacterium, Blautia, Bordetella, Borrelii, Brucella, Bulleidia, Citrobacter, Campylobacter, Chlamydia, Christensenellaceae, Clostridium, Coprococcus, Corynebacteria, Coriobacterium, Deltaproteobacteria, Desulfovibrio, Dialister, Ehrlichia, Enterobacter, Enterobacterium, Enterococcus, Erysipelotrichia, Erwinia, Escherichia, Eubacterium, Faecalibacterium, Firmicutes, Flavonifractor, Francisella, Fusobacterium, Helicobacter, Hemophilus, Klebsiella, Lactobacillus, Lactococcus, Lachnospiraceae, Legionella, Leptospira, Listeria, Methanobrevibacter, Moraxella, Mycobacterium, Mycoplasmi, Neisseria, Noecardia, Oribacterium, Oscillobacter, Oscillospira, Paeruginosa, Paraprevotella, Phascolarctobacterium, Porphyromonadaceae, Prevotella, Propionibacterium, Proteus, Proteobacterium, Pseudomonas, Rickettsia, Rikenellacea, Roseburia, Ruminococcus, Salmonella, Shigella, Spirrillum, Spirochetes, Staphylococcus, Stenotrophomonas, Streptobacillus, Streptomyces, Streptococcus, Succinivibrio, Sutterellaceae, Thermoanaerobacteria, Treponema, Veillonella, Vibrio* and/or *Yersenia.*

Furthermore, the intestinal and/or gastrointestinal species of bacteria is non-exclusively selected from: *Acinetobacter baumannii, Bacillus cereus, Bacillus anthracis, Bacillus subtilis, Bacteroides faecichinchillae, Bacteroides fragilis, Bacteroides thetaiotaomicron, Bacteroides vulgatus, Bartonella henselae, Bifidobacterium animalis, Bifidobacterium bifidum, Bifidobacterium breve, Bifidobacterium infantis, Bifidobacterium lactis, Bifidobacterium longum, Blautia hydrogenotorophica, Blautia wexlerae, Bordetella pertussis, Borrelia recurrentis, Borrelia hermsii, Borrelia turicatue, Borrelia burgdorferi, Campylobacter jejuni, Citrobacter fruendii, Citrobacter rodentium, Chlamydia psittaci, Chlamydia trachomatis, Chlamydia pneumoniae, Clostridium bolteae, Clostridium botulinum, Clostridium difficile, Clostridium leptum, Clostridium novyi, Clostridium perfringens, Clostridium ramosum, Clostridium septicum, Clostridium tetani, Coprococcus catus, Corynebacteria diptheriae, Desulfovibrio desulfuricans, Desulfovibrio fairfielddensis, Desulfovibrio piger, Ehrlichia chaffeensis, Enterococcus faecalis, Escherichia coli* (e.g., EHEC, EIEC, ETEC), *Eubacterium ventriosum, Erysipelothrix rhusiopathiae, Faecalibacterium prausnitzii, Firmicutes phyla, Flavonifractor plautii, Francisella tularensis, Helicobacter pylori, Hemophilus influenzae, Hemophilus parainfluenzae, Hemophilus aegyptus, Klebsiella pneumoniae, Lactobacillus acidophilus, Lactobacillus bulgaricus, Lactobacillus brevis, Lactobacillus casei, Lactobacillus farciminis, Lactobacillus gasseri, Lactobacillus helveticus, Lactobacillus paracasei, Lactobacillus plantarum, Lactobacillus reuteri, Lactobacillus rhamnosus, Lactobacillus salivarius, Lactococcus lactis, Legionella pneumophila, Leptospirex hemoragia, Leptospira icterohemorrhagiae, Listeria monocytogenes, Methanobrevibacter smithii, Moraxella catarrhalis, Mycobacterium tuberculosis, Mycobacterium leprae, Mycobacterium asiaticum, Mycobacterium intracellulare, Myco-bacterium avium-*intracellulars, *Myobacterium johnei, Mycobacterium avium, Mycobacterium smegmatis, Mycoplasma pneumoniae, Mycoplasma hominis, Neisseria men-* ingitidis, Neisseria gonorrhea, Pasteurella multocida, Propionibacterium acnes, Propionibacterium freudenreichii, Pseudomonas aeruginosa, Pseudomonas syringae, Rickettsia prowozekii, Rickettsia rickettsii, Rickettsia akari, Ruminococcus bromii, Ruminococcus obeum, Salmonella typhimurium, Salmonella typhi, Salmonella paratyphi, Salmonella schottmulleri, Salmonella hirshieldii, Shigella dysenteriae, Spirrillum minus, Staphylococcus aureus, Staphylococcus epidermidis, Stenotrophomonas maltophilia, Streptobacillus moniliformis, Streptococcus pneumoniae, Streptococcus mutans, Streptococcus oralis, Streptococcus parasanguis, Streptococcus pyogenes, Streptococcus viridans, Streptococcus coelicolor, Streptococcus agalactiae, Streptococcus bovis, Streptococcus thermophilus, Treponema pallidum, Treponema pertainue, Treponema carateum, Vibrio cholera, Vibrio parahaemolyticus, Yersenia pestis and/or Yersinia enterocolitica.

In the first step of the method according to the invention, a biological sample containing bacteria of at least one intestinal and/or gastrointestinal species of bacteria needs to be provided. The term "biological sample" refers to a material of a human and/or animal organism and/or a material that has had at least brief contact with a human and/or animal organism. It has been found essential that the biological sample contain bacteria of at least one intestinal and/or gastrointestinal species of bacteria, preferably 2, 3, 4, 5, 6, 7, 8, 9, 10, 11, 12, 13, 14, 15, 16, 17, 18, 19, 20 or more species of bacteria. Samples of this kind, such as samples containing cells and nuclei (DNA and/or RNA), e.g., saliva, urine, blood, stool, sweat, cellular tissue, organ puncture, organs, parts of organs, whole organisms (also dead), soil samples, water samples or similar samples, are known to a person skilled in the art.

In the next step of the method according to the invention, bacteriophages of at least one species of bacteriophages that are specific to the at least one intestinal and/or gastrointestinal species of bacteria need to be provided. The term "bacteriophages" or "species of bacteriophages" is known to a person skilled in the art and refers to infectious organic structures that spread outside of cells and can multiply within a cell. The cells serve as hosts and are essentially bacteria in the case of bacteriophages. Bacteriophages have a pronounced host specificity; i.e., in other words, they are specific to the at least one species of bacteria and use only those bacteria for which they are specific to proliferate and multiply.

The essential aspect is that the bacteriophages used for the method according to the invention comprise at least one nucleic acid functionally associated with a promotor and/or a regulatory element or have a promotor and/or a regulatory element in combination with a nucleic acid, the nucleic acid coding either for an antibacterial nucleic acid molecule, a bacterial polypeptide and/or a fragment thereof. Preferably, the bacteriophages comprise a nucleic acid with at least 2, 3, 4, 5, 6, 7, 8, 9, 10, 11, 12, 13, 14, 15, 16, 17, 18, 19, 20 or more promotors and/or regulatory elements. The nucleic acid sequences coding for promotors or regulatory sequences are sufficiently known to the person skilled in the art.

A person skilled in the art understands that the terms "nucleic acids", "genes", "DNA", "RNA", "mRNA", "cRNA", "miRNA" and the compounds "nucleic acid sequence" and "nucleic acid molecule" are used as exchangeable synonyms for each other to describe deoxyribonucleotides or ribonucleotides and polymers thereof, either single-stranded or double-stranded.

The terms "promotor" and regulatory sequence" or "regulatory element" are also known to the person skilled in the art and refer to nucleic acid sequences of the DNA that enable and/or enhance the expression, i.e., the transcription, of a gene into mRNA. In this case, regulatory elements can be enhancer elements, for example, i.e., binding sites for growth factors, hormones, oncogenes and/or the like.

A person skilled in the art further understands that the terms "polypeptide", "peptide", "amino acids" and "protein" are used as exchangeable synonyms for each other in order to describe a polymer of amino acid residues. Naturally occurring amino acids are amino acids that are encoded by the genetic code and amino acids that can be modified later. Polypeptides can be present as reserve substances, as a transport and/or signal molecule, as a structural molecule, as a protection and/or defense molecule and/or as a metabolically active molecule and can fulfil different functions within and/or outside of a cell or in the organism. For example, polypeptides can have an antibacterial effect and thus counteract the biology of the bacteria because of their properties or functions.

In the scope of the method according to the invention, at least one antibacterial nucleic acid molecule, an antibacterial polypeptide and/or a fragment thereof is/are provided; preferably, the bacteriophages can also encode 2, 3, 4, 5, 6, 7, 8, 9, 10, 11, 12, 13, 14, 15, 16, 17, 18, 19, 20 or more antibacterial nucleic acid molecules, antibacterial polypeptides and/or fragments thereof. Antibacterial nucleic acid molecules can originate from the field of the RNAs species and can be functional mRNA or miRNA, for example. Polypeptides can be present as simple linear polypeptides or as folded structural proteins. Molecules that act as toxins, growth-inhibiting substances and enzymes or molecules inhibiting mitosis are possible proteins. Nucleic acid molecules, such as RNA molecules, that inhibit metabolic processes, interfere with mitosis or promote malfunctions of the biological processes within the bacteria are possible nucleic acid molecules.

In the scope of the method according to the invention, a nucleic acid sequence that encodes a nucleic acid molecule, a polypeptide and/or a fragment thereof that is identical to said antibacterial nucleic acid sequence or the antibacterial polypeptide by at least 50% is conceivable. Preferably, a nucleic acid sequence identical to said antibacterial nucleic acid sequence or the antibacterial polypeptide by at least 55%, at least 60%, at least 65%, at least 70%, at least 75%, at least 80%, at least 85%, at least 90%, at least 95%, at least 96%, at least 97%, at least 98%, at least 99% or 100% is also conceivable. The nucleic acid sequence is a naturally occurring nucleic acid sequence or a not naturally occurring nucleic acid sequence already existing in bacteriophages or having been introduced into the bacteriophages in question by molecular biological processes, for example. For instance, these molecular biological processes can include in-vivo and/or in-vitro recombination, gene transfer, CRISPR/Cas, TALEN or the like.

The bacteriophages can belong to the order Caudovirales, Ligamenvirales or the like. Preferably, the bacteriophage belongs to the family Ackermanviridae, Ampullaviridae, Bicaudaviridae, Clavaviridae, Corticoviridae, Fuselloviridae, Globuloviridae, Guttaviridae, Lipothrixviridae, Myoviridae, Plasmaviridae, Podoviridae, Portogloboviridae, Rudiviridae, Salterprovirus, Sphaerolipoviridae, Siphoviridae, Tectiviridae, Tristomaviridae, Turriviridae, Inoviridae, Microviridae, Spiraviridae, Pleolipoviridae, Cystoviridae or Leviviridae. In the scope of the invention, it is conceivable for bacteriophages of at least one species of bacteriophages, preferably of 2, 3, 4, 5, 6, 7, 8, 9, 10, 11, 12, 13, 14, 15, 16, 17, 18, 19, 20 or more species of bacteriophages, to be provided. Furthermore, it is conceivable for the bacteriophages of a species of bacteriophages to be specific to at least one and preferably to 2, 3, 4, 5, 6, 7, 8, 9, 10, 11, 12, 13, 14, 15, 16, 17, 18, 19, 20 or more intestinal and/or gastrointestinal species of bacteria. A specific selection of a suitable bacteriophage for the corresponding species of bacteria is known to the person skilled in the art and can be easily selected from databases, for example.

In the next step of the method according to the invention, the biological sample needs to be contacted with the bacteriophages and incubated. The contacting can take place by dropwise application, injection, placement and/or another method for contacting bacteriophages with the biological sample known to the person skilled in the art.

The term "incubating" in the context of the method according to the invention refers to a method step in which the biological sample is incubated together with the bacteriophages for a certain period of time, during which a reproduction cycle of the bacteriophages within the biological sample containing the bacteria of the at least one species of bacteria specific to the bacteriophages occurs, preferably under the appropriate conditions, which are known to a person skilled in the art. This method step comprises not only incubating a biological sample with bacteriophages but also monitoring the incubation until the population of the at least one species of bacteria has been reduced by at least 70%. The procedure of monitoring is sufficiently known to the person skilled in the art and can take place based on a set length of time or on the experience of the person skilled in the art, e.g., by observing the sample. Alternatively, a color indication or another optically visible indication that indicates that a reduction of the population of the species of bacteria by at least 70% has been achieved can be provided. This can take place by reaching the intended bacterial density or by means of a chemical and/or biochemical indicator, e.g., by means of a stain, a color change of the stain or a loss in color. The steps of incubating and monitoring can take place alternately until the species of bacteria has been reduced by at least 70%.

In the scope of the invention, it has proven advantageous for the reduction of the population of the species of bacteria to be at least 70%. Preferably, the reduction of the population can also be greater than 70%, e.g., at least 75%, at least 80%, at least 85%, at least 90%, at least 95%, at least 95.5%, at least 96%, at least 96.5%, at least 97%, at least 97.5%, at least 98%, at least 98.5%, at least 99%, at least 99.1%, at least 99.2%, at least 99.3%, at least 99.4%, at least 99.5%, at least 99.6%, at least 99.7%, at least 99.8%, at least 99.9%, at least 99.95%, at least 99.99% or 100%, a reduction of the population of the species of bacteria by at least 70% being considered notable and a reduction of the population of the species of bacteria by at least 95% being considered significant. The person skilled in the art knows that a reduction is seldom 100%; however, 100% can very well be achieved if suitable bacteriophages are used in a suitable biological sample.

Moreover, the person skilled in the art recognizes the success of the method in a reduction of the population of the species of bacteria of 70% to 100%, which establishes a sufficient antibacterial effect and therefore a sufficient reduction of the intestinal and/or gastrointestinal species of bacteria within the biological sample. In this case, the reduction of the population of the species of bacteria can be used as a measure of the effectiveness or the success of a therapy based on the use of the bacteriophage in question. Alternatively, a reduction of a species of bacteria that is contrary to the life or a biology of a desired species of bacteria beneficial to a therapy can be aimed at. Thus, a survival or a growth of this species of bacteria can be achieved by reducing the species of bacteria counteracting it but specific to the bacteriophages. This is based on the assumption that a growth of a population of a desired species of bacteria beneficial to a therapy can ultimately have the same effect on an organism as the reduction of a population of a species of bacteria specific to the bacteriophages.

By means of the method according to the invention, it is thus possible for the population of at least one intestinal and/or gastrointestinal species of bacteria to be reduced specifically, effectively, with few side effects, in a well-tolerated manner, without hazards to health, permanently and long-term within a biological sample without damaging and/or affecting bacteria or other cells tissue and/or organisms within the same biological sample for which the bacteriophages have no specificity. In this manner, damage to other species of bacteria and to fungi, tissue and/or organs in the human and/or animal organism is avoided entirely contrary to the use of measures known from the state of the art. Thus, the method according to the invention can be performed not only reliably and cost efficiently but also quickly and simply, even more so since the few method steps can be executed in a standardized manner and a high success rate is achieved by a notable (more than 70% reduction) or significant (more than 95% reduction) reduction of the species of bacteria. Moreover, the method can be executed by simple means and the person skilled in the art merely needs known devices for providing the biological sample and the bacteriophage, for contacting and incubating the same and for evaluating the reduction of the species of bacteria in question within the population.

Advantageous embodiments of the invention, which can be realized individually or in combination, are indicated in the dependent claims.

In an embodiment of the invention, step c) can be followed by an evaluation of the reduction of the population of the intestinal and/or gastrointestinal species of bacteria. The term "evaluation" is understood by the person skilled in the art and refers to the analysis, interpretation and/or assessment of step c). Since a reduction of the population of the species of bacteria by at least 70% has been monitored prior, this method step serves in particular to verify the achieved reduction and, optionally, to log the result by producing written documentation, photographs and film recordings, collecting and documenting data on counts, density measurements, growth determinations or similar methods and can be referred to for statistics regarding the repeated execution of the method according to the invention. Also, the vitality or the viability of the bacteria remaining in the biological sample, which have not been killed or have been killed insufficiently by the bacteriophages, can be determined in this step. Additionally, the vitality of the bacteria for which the bacteriophages in question have no specificity can be determined. Common methods for this purpose are also known to the person skilled in the art.

Furthermore, in step b), the nucleic acid can have two or more promotors and/or regulatory elements and/or the nucleic acid can encode nucleic acid sequences for two or more nucleic acid molecules, polypeptides and/or fragments thereof. Preferably, the nucleic acid has 2, 3, 4, 5, 6, 7, 8, 9, 10, 11, 12, 13, 14, 15, 16, 17, 18, 19, 20 or more promotors and/or regulatory elements. Further preferably, the nucleic acid codes for 2, 3, 4, 5, 6, 7, 8, 9, 10, 11, 12, 13, 14, 15, 16, 17, 18, 19 or 20 nucleic acid molecules, polypeptides and/or fragments thereof. These nucleic acid molecules, polypeptides and/or fragments thereof can have an antibacterial effect for one or more species of bacteria; in this context, it is preferred for bacteriophages having such a nucleic acid to be able to infect multiple species of bacteria. Moreover, the nucleic acid sequences can be specific to the killing of one species of bacteria. The essential aspect is that a particularly strong activation of the expression of the nucleic acid and thus a particularly increased and efficient production of the antibacterial nucleic acid, the antibacterial nucleic acid molecule, the antibacterial polypeptide and/or the fragment thereof can be achieved. A bacteriophage having such a nucleic acid can particularly efficiently contribute to the reduction of the population of the species of bacteria and can, for example, significantly accelerate or significantly shorten step c) of the method according to the invention (the incubation). This leads to an increase in the efficiency of the method and to a reduction of the duration and/or costs of performing the method.

In an embodiment of the method, the intestinal and/or gastrointestinal species of bacteria can be anaerobic and/or aerobic and the species of bacteria can belong to *Acidaminococcaceae, Actinobacteria, Actinomycineae, Alistipes, Bacteroides, Bacteroidetes, Bifidobacterium, Clostridium, Coprococcus, Coriobacterium, Desulfovibrio, Enterobacterium, Enterococcus, Escherichia, Erysipelotrichia, Firmicutes, Fusobacterium, Lactobacillus, Lachnospiracea, Paraprevotella, Porphyromonadaceae, Prevotella, Propionibacterium, Proteobacteria, Rikenellacea, Ruminococcus, Streptococcus, Thermoanaerobacteria* or *Veillonella*.

The terms "aerobic" and "anaerobic" are sufficiently known to the person skilled in the art and describe a preferred biology of the organism in question. An "aerobic" biology means that the organism needs atmospheric oxygen or is dependent on oxygen from the air to live. On the other hand, "anaerobic" means a biology not requiring oxygen; i.e., the organism in question can maintain its molecular metabolism without oxygen. A difference is made between "obligate", "tolerant" and "facultative" aerobic or anaerobic organisms, the person skilled in the art understanding that "obligate" means an exclusively aerobic or anaerobic biology excluding the other oxygen situation. "Tolerant", on the other hand, means that the organisms live aerobically or anaerobically but tolerate the opposite oxygen condition at least for some time. Finally, the term "facultative" means that, for example, anaerobic organisms do metabolize accordingly in principle but can switch to an aerobic metabolism in the presence of oxygen and vice-versa. Thus, species of bacteria can have an exclusively aerobic or an exclusively anaerobic biology or a combination thereof.

In an embodiment of the method, the psychological, neurodegenerative and/or neurological illness and/or disorder can be an affective disorder, such as mania, hypomania, depression, such as fatigue syndrome, chronic fatigue syndrome, reduced self-worth and/or a perception of being appreciated less by the environment, a depressive disorder, such as recurring depressive disorder, a bipolar disorder and/or a persisting affective disorder, such as cyclothymia and/or dysthymia, a personality disorder, such as a multiple, paranoid, schizoid, dissocial, emotionally unstable, histrionic, anankastic (obsessive-compulsive), anxious (avoidant), dependent (asthenic) and/or other personality disorder, such as eccentric, insecure, narcissist, passive-aggressive, psychoneurotic and/or immature, a hallucination, an amnesia, a behavioral disorder, drug abuse, such as abuse, addiction, dependence, withdrawal syndrome and/or withdrawal symptoms, urticaria, a developmental disorder, such as dyslalia, a speech disorder (expressive and/or receptive), dyslexia, isolated spelling disorder, dyscalculia, dyspraxia and/or a mixed disorder of scholastic skills, a social disorder, such as separation anxiety, social phobia, sibling rivalry, attachment disorder, mutism (elective, selective, total and/or akinetic), non-organic enuresis, non-organic encopresis, feeding disorder, pica, stereotyped movement disorder, stuttering, cluttering and/or other behavioral and/or emotional disorders with onset specific to childhood and adolescence, such as nose-picking, nail-biting and/or thumb-sucking, an emotional disorder, a stress disorder, such as post-traumatic stress disorder, a dissociative disorder, such as fugue, poriomania, dromomania, conversion hysteria, Ganser syndrome, pseudo debility, obsession and/or conversion, a somatoform disorder, such as somatoform pain disorder, Briquet disorder and/or psychogenic disorders, such as dysphagia, pruritus, teeth-grinding and/or hyperventilation, a neurotic disorder, such as neurasthenia, depersonalization, derealization, writer's cramp, Dhat syndrome, psychasthenia and/or psychogenic syncope, a body dysmorphic disorder, a phobia, such as social phobia, a phobic disorder, an anxiety disorder, such as generalized anxiety disorder, agoraphobia, social phobia, acrophobia and/or a specific other phobia, a panic disorder, an obsessive-compulsive disorder, such as compulsive acts and/or obsessional thoughts, schizophrenia, a schizotypal disorder, a schizoaffective disorder, a delusional disorder, a psychosis, a psychotic disorder, such as a transient or non-organic psychotic disorder, an eating disorder, such as Anorexia nervosa, bulimia, binge eating and/or pica, a sleep disorder, such as parasomnia, primary insomnia, somnambulism and/or Pavo nocturnus, a sexual dysfunction, such as lack or loss of sexual desire, hypersexuality, nymphomania, satyriasis and/or psychogenic sexual dysfunction, such as vaginismus, anorgasmia, hyporgasmia, impotence and/or dyspareunia, a gender identity disorder, such as transsexualism and/or dual-role transvestism, a disorder of sexual preference, such as fetishism, fetishistic transvestism, exhibitionism, voyeurism, pedophilia, sadomasochism, multiple disorders of sexual preference and/or other disorders of sexual preference, such as frotteurism and/or necrophilia, post-partum depression, a tic disorder, Asperger syndrome, attention deficit hyperactivity disorder, alcohol addiction, autism, such as childhood autism or atypical autism, Parkinson disease, Alzheimer disease, dementia, a motor neuron disease, such as amyotrophic lateral sclerosis, primary lateral sclerosis, spastic paraplegia, progressive muscular atrophy, spinal muscular atrophy, progressive bulbar palsy and/or pseudobulbar palsy, a (neuro)degenerative cerebellar disorder, such as hereditary ataxia, epilepsy, multiple sclerosis, irritable bowel syndrome, localized pain or pain throughout the body, such as headache and/or limb pain and/or migraine, a nerve injury, a tumor, localized, metastasized or throughout the body, preferably in the brain, the spinal cord and/or the peripheral nerves, a vascular disorder, such as ischemic brain infarction, intracerebral hemorrhage, myocardial infarction, hypertension, a vascular disease, such as Raynaud syndrome and/or a localized functional vascular disorder, an inflammatory organic vascular disease, such as Endangiitis obliterans and/or Periateriitis nodosa, and/or a degenerative vascular disease, such as arteriosclerotic vascular disease, aneurysm, thrombosis, embolism and/or phlebitis, stroke and/or a mixture thereof. A person skilled in the art is aware that said psychological, neurodegenerative and/or neurological illness and/or disorder can occur on its own or in direct or indirect correlation with a known or unknown psychological, neurodegenerative and/or neurological illness and/or disorder mentioned above.

It is assumed that the definition and/or the explanations of the terms mentioned above apply to all aspects described hereinafter in this description unless indicated otherwise.

According to the invention, a kit for implementing the method according to the invention is furthermore proposed, the kit comprising a) a container containing bacteriophages of at least one species of bacteriophages that are specific to at least one intestinal and/or gastrointestinal species of bacteria, the intestinal and/or gastrointestinal species of bacteria directly or indirectly influencing a psychological, neurodegenerative and/or neurological illness and/ or disorder of a host organism, and that comprise at least one nucleic acid functionally associated with a promotor and/or a regulatory element; and b) instructions for carrying out the method.

The term "kit" as used herein refers to a collection of the components mentioned above (kit of parts), which are preferably provided separately or within a single container.

The expression "instruction for carrying out the method" refers to a numerical, written and/or graphical representation of the description by means of which the implementation of the method aim according to the invention is facilitated. They can preferably be in the form of a hand book or can be provided by a computer program, such as an application. Furthermore, the computer program can have an implemented algorithm capable of carrying out the determination, the comparison and/or the result thereof to which reference is made in the methods of the present invention. The computer program can be provided on a data storage medium or device, such as an optical storage medium (e.g., compact disc) or directly on a computer or a data processing device. Moreover, the instructions can preferably comprise standards for quantities as they are known to a person skilled in the art. Additionally, the instructions comprise requirements for the storage and the disposal of the container and the biological sample. Also, the instructions for implementing the method can comprise tables, registers, databases or excerpts thereof on species of bacteria and species of bacteriophages known to the person skilled in the art, wherein the specificity and/or the efficiency of the species of bacteriophages can be indicated.

Furthermore, the invention proposes a bacteriophage comprising at least one nucleic acid functionally associated with a promotor and/or with a regulatory element, the bacteriophage being specific to the at least one intestinal and/or gastrointestinal species of bacteria, the intestinal and/or gastrointestinal species of bacteria directly or indirectly influencing a psychological, neurodegenerative and/or neurological illness and/or disorder of a host organism and wherein the nucleic acid is selected from the group comprising:

a) a nucleic acid sequence coding for at least one antibacterial nucleic acid molecule; and b) a nucleic acid sequence encoding a nucleic acid molecule that is identical to the nucleic acid molecule encoded by the nucleic acid sequences from a) by at least 50%; and c) a nucleic acid sequence coding for at least one antibacterial polypeptide; and d) a nucleic acid sequence encoding a polypeptide that is identical to the polypeptide encoded by the nucleic acid sequences from c) by at least 50%; and e) a nucleic acid sequence for a fragment of a nucleic acid from a), b), c) or d), the fragment encoding a nucleic acid molecule or a polypeptide.

The bacteriophage according to the invention has been described in detail above. The nucleic acid sequence is a naturally occurring nucleic acid sequence or a not naturally occurring nucleic acid sequence already existing in the bacteriophage or having been introduced into the bacteriophage by molecular biological processes, for example. For instance, these molecular biological processes can refer to in-vivo and/or in-vitro recombination, gene transfer, CRISPR/Cas, TALEN or the like, as is known to a person skilled in the art.

In an embodiment, it is conceivable for the nucleic acid to have two or more promotors and/or regulatory elements and/or for the nucleic acid to encode nucleic acid sequences for two or more nucleic acid molecules, polypeptides and/or fragments thereof. The essential aspect is that a particularly strong activation of the expression of the nucleic acid and therefore a particularly increased and efficient production of the antibacterial nucleic acid, the antibacterial nucleic acid molecule, the antibacterial polypeptide and/or the fragment thereof are achieved. The bacteriophage having such a nucleic acid can contribute particularly efficiently to the reduction of the population of the intestinal and/or the gastrointestinal species of bacteria or to the reduction of a species of bacteria contrary to the biology of this species of bacteria. Furthermore, it is conceivable for the bacteriophage having such a nucleic acid to be able to infect multiple species of bacteria.

In yet another embodiment, it is conceivable for the intestinal and/or gastrointestinal species of bacteria to be anaerobic and/or aerobic. The classification of the species of bacteria has been described in detail above.

The psychological, neurodegenerative and/or neurological illness and/or disorder according to the invention has been described in detail above.

Furthermore, the invention proposes bacteriophages and/or a pharmaceutical composition comprising bacteriophages and at least one other ingredient as a drug for changing the composition of the gut microbiota, as a drug for preventing the development and/or decelerating the progression of the psychological, neurodegenerative and/or neurological illness and/or disorder and/or as a drug for treating the psychological, neurodegenerative and/or neurological illness and/or disorder, a bacterial infection, a metabolic illness, metabolic syndrome and/or cancer.

The expression "pharmaceutical composition" used herein refers to a mixture of bacteriophages, which have been defined in detail above, and at least one other ingredient. Preferably, other ingredients of this kind can be stabilizers, wetting agents, pharmaceutical carriers, pharmaceutically acceptable carriers, diluting agents, pharmaceutically acceptable diluting agents, additional pharmaceutical agents, separating agents and the like. Preferred diluting agents comprise water, alcohol, physiological saline solutions, buffers, such as phosphate-buffered saline solutions, syrup, oil, water, emulsions, different types of wetting agents and the like. The carrier has to be acceptable in the sense that it is compatible with the other ingredients of the composition and that it is not harmful to the host organism. The pharmaceutical carrier used can contain a solid, a gel or a liquid. Examples of solid carriers are lactose, terra alba, sucrose, talcum, gelatin, agar, pectin, acacia, magnesium stearate, stearic acid and the like. Similarly, the carrier or the diluting agent can contain a time delay material well known in the art, such as glycerol monostearate or glycerol distearate alone or with a wax. These suitable carriers comprise the carriers mentioned above and other carriers known in the professional field, such as Remington's Pharmaceutical Sciences, Mack Publishing Company, Easton, Pennsylvania, European Pharmacopoeia, Homeopathic Pharmacopoeia of the USA or HAB. The pharmaceutically acceptable diluting agent is selected in such a manner that the biological activity of the combination is not compromised. Examples of such diluting agents are distilled water, physiological saline solution, Ringer's solutions, dextrose solution and Hanks' solution. Moreover, the pharmaceutical composition can also contain other carriers, adjuvants or non-toxic, non-therapeutic, non-immunogenic stabilizers and the like.

The bacteriophages and/or the pharmaceutical composition are to be adapted for the use in question. Accordingly, it is assumed that the bacteriophages and/or the pharmaceutical composition are formulated for a systemic or a topic application depending on the intended method of administration. Preferably, the bacteriophages and/or the pharmaceutical composition are to be formulated for a systemic or a local application. Preferably, an oral administration, e.g., in the form of tablets, solutions and/or drinkable ampoules, or a topical application in gel form or an application by injection, e.g., as an active or passive vaccine, is intended. However, the bacteriophages and/or the pharmaceutical composition can also be administered in other ways, including dermal, intramuscular, subcutaneous, oral, rectal, retrograde and/or intravenous administration, depending on the type and the mode of action. The individually recommended exact dosage can basically depend on other parameters, which are well known to the person skilled in the art. For instance, children may receive a different dose than adults. The person skilled in the art can easily determine whether the dosage has to be adjusted with the help of various known calculation tools.

The expression "changing the composition of the gut microbiota" describes a process that is well known to the person skilled in the art and in which the at least one population of an intestinal and/or gastrointestinal species of bacteria that is part of the gut microbiota of the host organism is directly or indirectly increased, reduced, eliminated, inhibited and/or affected in another manner using the methods known to the person skilled in the art and as described in detail above. This can be measured per se by determining the number of bacteria in question or be determined relative to the other species of bacteria within the gut microbiota. Suitable methods for this purpose are known to the person skilled in the art.

The expression "preventing the development of the psychological, neurodegenerative and/or neurological illness and/or disorder" is also understood by a person skilled in the art and refers to the partial, full, short-term, permanent and/or long-term avoidance of the onset of the illness and/or disorder and/or its prevention/prophylaxis. It is preferably possible for this to be achieved by reducing at least one intestinal and/or gastrointestinal species of bacteria.

The expression "decelerating the progression of the psychological, neurodegenerative and/or neurological illness and/or disorder" is also understood by a person skilled in the art and refers to the partial, full, short-term, permanent and/or long-term maintenance of the achieved state and an improvement of the symptoms accompanying the psychological, neurodegenerative and/or neurological illness and/or disorder. It is preferably possible for this to be achieved by reducing at least one intestinal and/or gastrointestinal species of bacteria.

The bacteriophages and/or the pharmaceutical composition can be used as a drug for treating the psychological, neurodegenerative and/or neurological illness and/or disorder and illnesses in the medical fields of oncology, immunology, infectious diseases, dental, oral and orthodontic medicine, otorhinolaryngology, ophthalmology, neurology, gynecology, gastroenterology, endocrinology, psychiatrics, psychosomatics, orthopedics, pediatrics, surgery, urology and/or the like. Possible diagnoses that can indicate a use of the bacteriophages and/or the pharmaceutical composition aside from the psychological, neurodegenerative and/or neurological illness and/or disorder mentioned include metabolic syndrome, diabetes mellitus type 2, gallbladder diseases, chronic illnesses of the gastrointestinal tract, chronic bowel inflammations, elevated cholesterol levels, hyperacidity, hypertension, dyslipidemia, difficulty breathing, sleep apnoea, coronary heart diseases, arthrosis, gout, cancer, such as uterine, breast, cervical, pancreatic, liver, stomach, lymphatic, skin, blood, intestinal, prostate and/or gallbladder cancer, sex hormone disorders, reduced libido, pain, increased risk of thrombosis and embolism and/or increased risk during surgery and anaesthesia. Preferably, the aim in each case is to reduce at least one intestinal and/or gastrointestinal species of bacteria and thus change the composition of the gut microbiota and to prevent and/or decelerate the development and/or the progression of the psychological, neurodegenerative and/or neurological illness and/or disorder as a primary or secondary success in order to thus obtain a good, preferably improved, prognosis for treating the illness in question and/or the ailment in question or even cure the same. A use of the bacteriophages and/or the pharmaceutical composition is possible irrespective of the actual illness. A success is seen in the reduction of at least one intestinal and/or gastrointestinal species of bacteria and/or the prevention of the development and/or the deceleration of the progression of the psychological, neurodegenerative and/or neurological illness and/or disorder alone.

The term "treatment" refers to any improvement of the human and/or animal organism occurring compared to an untreated human and/or animal organism, this improvement preferably being based on the reduction at least one intestinal and/or gastrointestinal species of bacteria, the change in the composition of the gut microbiota and/or the prevention of the development and/or the deceleration of the progression of the psychological, neurodegenerative and/or neurological illness and/or disorder of the human and/or animal organism. It is also conceivable for it to be cured. It is assumed that a treatment might not be successful in all human and/or animal organisms to be treated. However, the term presupposes that the treatment is successful for a statistically significant portion of the subjects (e.g., a cohort in a cohort study). The person skilled in the art can easily determine whether a portion is statistically significant with the aid of various known statistical evaluating instruments, e.g., determination of confidence intervals, p-value determination, student's t-test, Mann-Whitney test, etc. Preferred confidence intervals are at least 90%, at least 95%, at least 97%, at least 98% or at least 99%. The p-values are preferably 0.05, 0.01, 0.005 or 0.0001.

The term "drug" refers to bacteriophages and/or a pharmaceutical composition in a therapeutically effective dose, as mentioned in detail above. The pharmaceutical composition preferably contains bacteriophages, at least one pharmaceutically acceptable carrier and/or a diluting agent. The drug can be formulated for different routes of administration, which have been described in detail above. A therapeutically effective dose refers to the quantities required for changing the composition of the gut microbiota, for reducing at least one intestinal and/or gastrointestinal species of bacteria, for preventing the development and/or decelerating the progression of and/or for treating the diseases mentioned above. The therapeutic efficacy and toxicity can be determined in cell cultures or laboratory animals using pharmaceutical standard procedures, e.g., ED50 (the dose therapeutically effective for 50%) and LD50 (the dose lethal for 50%). The dosage ratio between therapeutic and toxic effects is the therapeutic index, which can be expressed as the ratio LD50/ED50. The dosage regime is determined by the treating physician and other clinical factors. As is known in medicine, the appropriate dosage depends on many factors, including size, body surface, age, the substance to be administered, sex, time and route of administration, general health and other medication administered at the same time, which are known to a person skilled in the art. The progress can be monitored by periodic assessment.

Furthermore, the invention proposes bacteriophages and/or a pharmaceutical composition comprising bacteriophages and at least one other ingredient for use in treating a metabolic disorder, a cardiovascular disorder, a bacterial infection, a metabolic illness, metabolic syndrome and/or cancer.

Furthermore, the invention proposes bacteriophages and/or a pharmaceutical composition comprising bacteriophages and at least one other ingredient for use in a therapeutic method or in a non-therapeutic method for changing the composition of the gut microbiota, in a therapeutic method or in a non-therapeutic method for preventing the development and/or decelerating the progression of the psychological, neurodegenerative and/or neurological illness and/or disorder and/or in a therapeutic method or in a non-therapeutic method for treating a metabolic disorder a cardiovascular disorder, a bacterial infection, a metabolic illness, metabolic syndrome and/or cancer.

The psychological, neurodegenerative and/or neurological illness and/or disorder has been described in detail above. In an embodiment of the invention, the bacterial infection can be a bacterial infection of the respiratory tract, the teeth, the mouth, the jaw, the eye, the musculoskeletal system, the blood, the gastrointestinal tract, preferably a bacterial infection of the colon, the small intestine, the duodenum, the stomach, the liver, the gallbladder and/or the pancreas, the skin, the cardiovascular system, the hormonal balance, the mind, the immune system, the nervous system, the metabolism, wounds and/or the urogenital tract.

The term "gastrointestinal tract" is understood by a person skilled in the art and refers to organs of the human and/or animal organism serving the consumption, the breakup, the transport and/or the processing of nutrients with the aim of making the nutrients digestible to the human and/or animal organism, the intestine contributing substantially to the regulation thereof, in particular through the gut microbiota.

The features described herein can be realized each on their own or in any combination with each other. The invention is not limited to the illustrative examples.

I claim:

1. A method for reducing the population of at least one intestinal and/or gastrointestinal species of bacteria, the method comprising the following steps:
   a) providing a biological sample containing bacteria of at least one intestinal and/or gastrointestinal species of bacteria, the intestinal and/or gastrointestinal species of bacteria directly or indirectly influencing a psychological, neurodegenerative and/or neurological illness and/or disorder of a host organism; and b) providing bacteriophages of at least one species of bacteriophages that are specific to the intestinal and/or gastrointestinal species of bacteria and that comprise at least one nucleic acid functionally associated with a promoter and/or a regulatory element, the nucleic acid being selected from the group comprising:
      i. a nucleic acid sequence coding for at least one antibacterial nucleic acid molecule; and
      ii. a nucleic acid sequence encoding a nucleic acid molecule that has at least 90% sequence identity to the nucleic acid molecule encoded by the nucleic acid sequences from i); and
      iii. a nucleic acid sequence coding for at least one antibacterial polypeptide; and
      iv. a nucleic acid sequence encoding a polypeptide that has at least 90% sequence identity to the polypeptide encoded by the nucleic acid sequences from iii); and
      v. a nucleic acid sequence for a fragment of a nucleic acid from i), ii), iii) or iv), the fragment encoding a nucleic acid molecule or a polypeptide; and
   c) contacting and incubating the biological sample with the bacteriophages, the incubation continuing until the population of the intestinal and/or gastrointestinal species of bacteria has been reduced by at least 70%;
      wherein the intestinal and/or gastrointestinal species of bacteria is anaerobic and/or aerobic and wherein the species of bacteria belongs to *Alistipes, Bifidobacterium, Campylobacter, Chlamydia, Desulfovibrio, Enterobacter, Enterobacterium, Faecalibacterium, Helicobacter, Klebsiella, Porphyromonadaceae, Prevotella, Proteus, Roseburia, Ruminococcus, Shigella, Spirochetes, Streptococcus, Treponema* or *Veillonella*; and wherein the psychological, neurodegenerative and/or neurological illness and/or disorder is a depression, depressive disorder, eating disorder, Parkinson disease, Alzheimer disease, dementia, and/or a mixture thereof.

2. The method according to claim 1, wherein step c) is followed by an evaluation of the reduction of the population of the intestinal and/or gastrointestinal species of bacteria.

3. The method according to claim 1, wherein the nucleic acid has two or more promoters and/or regulatory elements and/or wherein the nucleic acid encodes nucleic acid sequences for two or more nucleic acid molecules, polypeptides and/or fragments thereof.

4. A bacteriophage comprising at least one nucleic acid functionally associated with a promoter and/or a regulatory element, the bacteriophage being specific to at least one intestinal and/or gastrointestinal species of bacteria, the intestinal and/or gastrointestinal species of bacteria directly or indirectly influencing a psychological, neurodegenerative and/or neurological illness and/or disorder of a host organism, and the nucleic acid being selected from the group comprising:
   a) a nucleic acid sequence coding for at least one antibacterial nucleic acid molecule; and
   b) a nucleic acid sequence encoding a nucleic acid molecule that has at least 90% sequence identity to the nucleic acid molecule encoded by the nucleic acid sequences from a); and
   c) a nucleic acid sequence coding for at least one antibacterial polypeptide; and
   d) a nucleic acid sequence encoding a polypeptide that has at least 90% sequence identity to the polypeptide encoded by the nucleic acid sequences from c); and e) a nucleic acid sequence for a fragment of a nucleic acid from a), b), c) or d), the fragment encoding a nucleic acid molecule or a polypeptide;

wherein the intestinal and/or gastrointestinal species of bacteria is anaerobic and/or aerobic and wherein the species of bacteria belongs to *Alistipes, Bifidobacterium, Campylobacter, Chlamydia, Desulfovibrio, Enterobacter, Enterobacterium, Faecalibacterium, Helicobacter, Klebsiella, Porphyromonadaceae, Prevotella, Proteus, Roseburia, Ruminococcus, Shigella, Spirochetes, Streptococcus, Treponema* or *Veillonella,* and wherein the psychological, neurodegenerative and/or neurological illness and/or disorder is a depression, depressive disorder, eating disorder, Parkinson disease, Alzheimer disease, dementia, and/or a mixture thereof.

5. The bacteriophage according to claim 4, wherein the nucleic acid has two or more promoters and/or regulatory elements and/or wherein the nucleic acid encodes nucleic acid sequences for two or more nucleic acid molecules, polypeptides and/or fragments thereof.

6. The bacteriophages according to claim 4 and/or a pharmaceutical composition comprising bacteriophages according to claim 4 and at least one other ingredient for use as a drug for changing the composition of the gut microbiota, as a drug for preventing the development and/or decelerating the progression of the psychological, neurodegenerative and/or neurological illness and/or disorder and/or as a drug for treating the psychological, neurodegenerative and/or neurological illness and/or disorder.

7. The bacteriophages according to claim 4 and/or a pharmaceutical composition comprising bacteriophages according to claim 4 and at least one other ingredient for use in treating the psychological, neurodegenerative and/or neurological illness and/or disorder.

8. The bacteriophages according to claim 4 and/or a pharmaceutical composition comprising bacteriophages according to claim 4 and at least one other ingredient for use in a therapeutic method or in a non-therapeutic method for changing the composition of the gut microbiota, in a therapeutic method or in a non-therapeutic method for preventing the development and/or decelerating the progression of the psychological, neurodegenerative and/or neurological illness and/or disorder and/or in a therapeutic method or in a non-therapeutic method for treating the psychological, neurodegenerative and/or neurological illness and/or disorder.

* * * * *